US008672850B1

(12) United States Patent
Miller

(10) Patent No.: US 8,672,850 B1
(45) Date of Patent: Mar. 18, 2014

(54) FOCUSING OF A TWO-DIMENSIONAL ARRAY TO PERFORM FOUR-DIMENSIONAL IMAGING

(75) Inventor: Steven Charles Miller, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 1322 days.

(21) Appl. No.: 11/652,452

(22) Filed: Jan. 11, 2007

(51) Int. Cl.
*A61B 8/00* (2006.01)

(52) U.S. Cl.
USPC .......................... 600/447; 600/437; 600/443

(58) Field of Classification Search
USPC ............ 600/437, 443, 447; 73/596, 625, 627, 73/628, 632, 633
See application file for complete search history.

(56) References Cited

U.S. PATENT DOCUMENTS

| 5,520,187 | A | 5/1996 | Snyder |
| 5,897,501 | A | 4/1999 | Wildes et al. |
| 2004/0220474 | A1* | 11/2004 | Abend et al. ................. 600/437 |
| 2005/0251040 | A1* | 11/2005 | Relkuntwar et al. ......... 600/437 |

OTHER PUBLICATIONS

Elevation Beam Profile Control With Bias Polarity Patterns Applied to Microfabricated Ultrasound Transducers, Chris Daft, Paul Wagner, Satchi Panda and Igal Ladabaum, 2003 IEEE Ultrasonics Symposium—1578.

\* cited by examiner

*Primary Examiner* — Tse Chen
*Assistant Examiner* — Mark Remaly
(74) *Attorney, Agent, or Firm* — McAndrews, Held & Malloy, Ltd.; David Bates

(57) ABSTRACT

Certain embodiments of the present technology provide systems and methods for focusing a two dimensional phased array to perform four dimensional ultrasonic imaging. For example, certain embodiments of the present technology provide an ultrasonic imaging system comprising: a transducer configured to emit ultrasonic beams and detect reflected ultrasonic beams; a transmitter configured to transmit a first ultrasonic beam using a first focusing function and transmit a second ultrasonic beam that has a quadrature relationship to the first ultrasonic beam using a second focusing function; a receiver configured to acquire a first acoustic line based on a reflected first ultrasonic beam using a first focusing function and acquire a second acoustic line based on a reflected second ultrasonic beam using a second focusing function; and a beamformer configured to combine acoustic lines acquired by a receiver to create a beam pattern.

15 Claims, 2 Drawing Sheets

FOCUSING OF A TWO-DIMENSIONAL ARRAY TO PERFORM FOUR-DIMENSIONAL IMAGING

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Embodiments of the present technology generally relate to ultrasonic imaging. More particularly, embodiments of the present technology relate to focusing a two-dimensional ("2D") phased array to perform four-dimensional ("4D"), also known as real-time three-dimensional ("real-time 3D"), ultrasonic imaging.

Ultrasound is sound having a frequency that is higher than a normal person can hear, for example, higher than 20,000 Hz. Ultrasonic imaging utilizes ultrasound waves to create an image. That is, ultrasonic imaging systems transmit ultrasonic sound waves, for example, in the range of 2 to 13 MHz, into a subject, such as a patient, receive echoes that are reflected back from the subject and interpret those echoes, thereby creating an image.

Ultrasonic imaging systems utilize transducers to transmit and detect ultrasound. A transducer is a device that converts a signal from one form to another. Some ultrasonic transducers have more than one, also known as an array, of transducer elements. Such transducers are known as phased array transducers. In phased array transducers, each transducer element can transmit ultrasound waves. Likewise, in phased array transducers, each transducer element can detect echoed ultrasound waves.

A focal zone is an area at which transmitted ultrasound waves are focused. It is desirable to transmit ultrasound waves so as to achieve peak pressure at the focal zone. When using phased array transducers, achieving peak pressure at a focal zone occurs when each transmitted ultrasound wave reaches the focal zone at the same time or in-phase. In order to allow each ultrasound wave transmitted from a phased array transducer to reach the focal zone at the same time or in-phase, the transducer can vary the amplitude and/or phase of the wave transmitted from each transducer element based on the location of the transducer element and the location of the focal zone. This practice is known as beamforming.

Beamforming can also be used in connection with receiving echoed ultrasound waves. That is, waves that are reflected from the focal zone at the same time and which arrive at transducer elements at separate times can be amplified or delayed in separate processing channels and then combined in a beamformer to create the best beam possible. The beam is then used to create an image. Failure to properly beamform can result in large sidelobes and/or large temporal misalignment of pulses, both of which are undesirable because either can result in reduced image quality.

Forming a best possible image at all times for different anatomies and patient types is important to diagnostic imaging systems. Poor image quality may prevent reliable analysis of an image. For example, a decrease in image contrast quality may yield an unreliable image that is not usable clinically. Additionally, the advent of real-time imaging systems has increased the importance of generating clear, high quality images.

A 2D phased array can be used to produce 4D ultrasound images. However, a 2D phased array can have several thousand elements, and acquiring and controlling data from this many elements can be difficult and costly.

One type of transducer that has been used with a 2D phased array to produce 4D ultrasound images is a Capacitive Micromachined Ultrasonic Transducer ("cMUT"). CMUT's can convert electrical signals into acoustic signals, such as ultrasonic signals, and can also convert acoustic signals, such as ultrasonic signals, into electrical signals. CMUT's require a direct current ("DC") bias in order to operate.

As described in the article *Elevation Beam Profile Control With Bias Polarity Patterns Applied To Microfabricated Ultrasound Transducers*, Chris Daft, Paul Wagner, Satchi Panda and Igal Ladabaum, 2003 IEEE Ultrasonics Symposium-1578, beamforming of a 2D array can be performed in a separable method. For example, beamforming in the azimuthal direction can be performed using delay (and/or phase) and sum, and beamforming in the elevation direction can be performed using cMUT bias control. In such systems, the 2D array can be composed of an array of one-dimensional ("1D") transducer elements in the azimuth direction with bias functions applied in the elevation direction. The article expands upon those aspects of focusing a 2D phased array to perform 4D ultrasonic imaging and also discusses other aspects of focusing a 2D phased array to perform 4D ultrasonic imaging. However, the approach proposed by the article can result in large sidelobes due to the coarseness of the phase information and large temporal misalignment of pulses, either of which can result in reduced image quality.

Thus, there is a need for improved systems and methods for focusing a 2D phased array to perform 4D ultrasonic imaging, which systems and methods decrease sidelobe size and/or temporal misalignment of pulses, thereby providing improved image quality.

BRIEF SUMMARY OF THE INVENTION

Certain embodiments of the present technology provide an ultrasonic imaging system comprising: a transducer configured to emit ultrasonic beams and detect reflected ultrasonic beams; a transmitter configured to transmit ultrasonic beams emitted by the transducer; a receiver configured to receive reflected ultrasonic beams detected by the transducer; and a beamformer configured to create a beam pattern based on a plurality of received ultrasonic beams. For example, in certain embodiments, an ultrasonic imaging system can include a transmitter configured to transmit a first ultrasonic beam using a first focusing function and transmit a second ultrasonic beam that has a quadrature relationship to the first ultrasonic beam using a second focusing function. For example, in certain embodiments, an ultrasonic imaging system can include a receiver configured to acquire a first acoustic line based on a reflected first ultrasonic beam using a first focusing function and acquire a second acoustic line based on a reflected second ultrasonic beam using a second focusing function. For example, in certain embodiments, an ultrasonic imaging system can include a beamformer configured to combine acoustic lines acquired by a receiver to create a beam pattern.

Certain embodiments of the present technology provide a method for creating a beam pattern comprising: transmitting a first ultrasonic beam; transmitting a second ultrasonic beam that has a quadrature relationship to the first ultrasonic beam; receiving the first and second ultrasonic beams after they have been reflected; acquiring a first acoustic line based on the first reflected beam and acquiring a second acoustic line based on the second reflected beam; and combining the first and second acoustic lines to create a beam pattern. For example, in certain embodiments, a method for creating a beam pattern can include transmitting a first ultrasonic beam using a first focusing function; and transmitting a second ultrasonic beam that has a quadrature relationship to the first ultrasonic beam using a second focusing function. For example, in certain embodiments, a method for creating a beam pattern can include acquiring a first acoustic line based on the first reflected beam using a first focusing function and acquiring a second acoustic line based on the second reflected beam using a second focusing function. For example, in certain embodiments, a method for creating a beam pattern can include using a beam pattern to generate an image.

Figure 1:
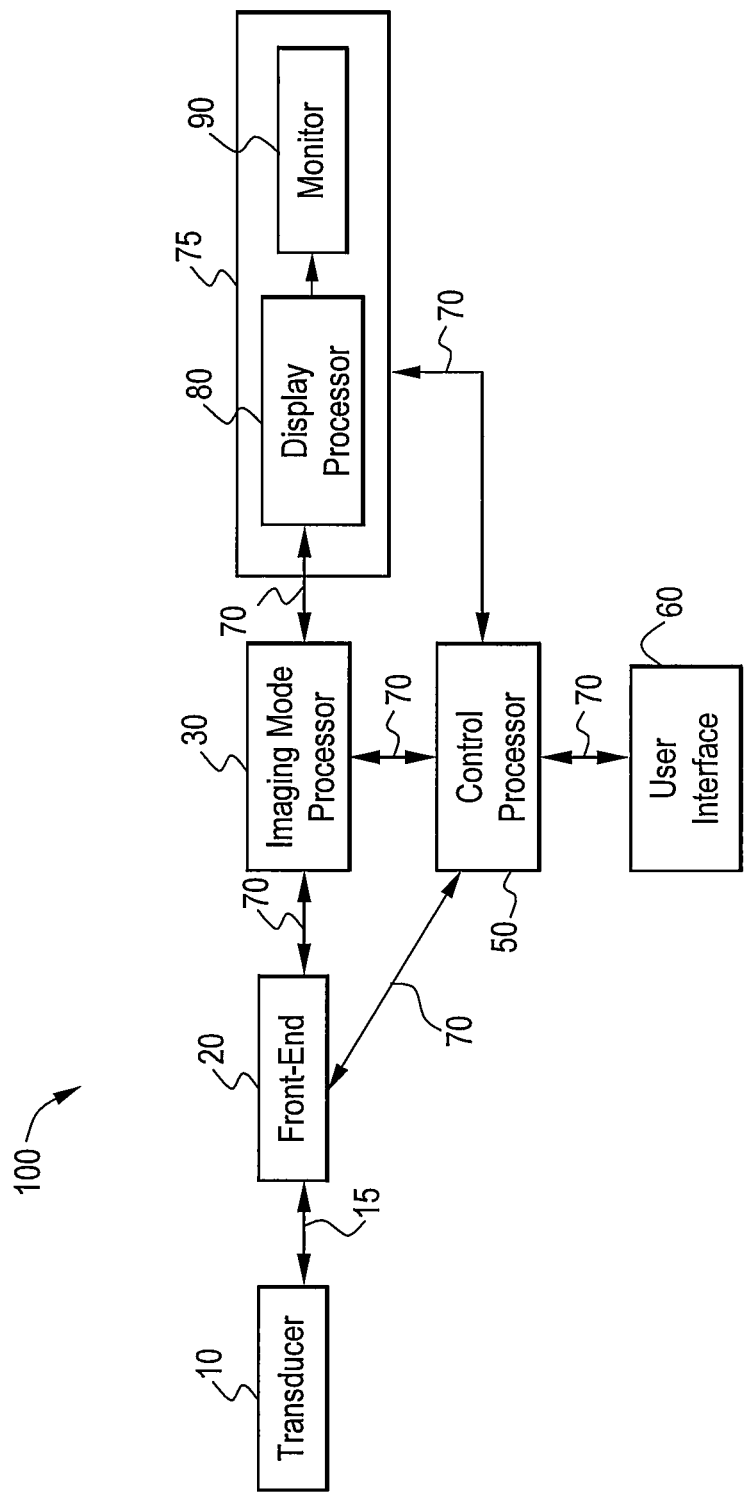
FIG. 1 illustrates a block diagram of an ultrasound imaging system used in accordance with an embodiment of the present technology.

The foregoing summary, as well as the following detailed description of embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EMBODIMENTS

FIG. 1 illustrates a block diagram of an ultrasound imaging system 100 used in accordance with an embodiment of the present technology. The system 100 includes a transducer 10, a front-end 20, an imaging mode processor 30, a user interface 60, a control processor 50, and a display 75. In certain embodiments, the imaging mode processor 30 and the control processor 50 may be part of a back-end system.

The transducer 10 and front-end 20 can be used together to create a beam pattern that is used to create an image. The transducer 10 can be used to transmit ultrasound waves into a subject by converting electrical analog signals to ultrasonic energy. The transducer 10 can also be used to detect ultrasound waves that are backscattered from the subject by converting ultrasonic energy to analog electrical signals. The front-end 20 can include a receiver, a transmitter and/or a beamformer. The front-end 20 can be used to create transmitted waveforms, beam patterns, receiver filtering techniques, and demodulation schemes that can be used for various imaging modes. The front-end 20 can interface with the transducer 10 via an analog interface 15. The front-end 20 can interface with the imaging mode processor 30 and the control processor 50 via a digital bus 70. The digital bus 70 can include several digital sub-buses. The digital sub-buses can have separate configurations and provide digital data interfaces to various parts of the ultrasound imaging system 100.

In certain embodiments, the transducer 10 can be a cMUT with a 2D phased array that is divided into two or more rows of elements in elevation. For example, in certain embodiments, the 2D phased array can be composed of 3 rows of 128 elements, where, via multiplexing circuitry, for example, 3 rows of 85 elements can be connected to a 255 channel beamformer. In such embodiments, the 85 element azimuthal aperture extent can be shifted among the 128 elements by multiplexer control, for example. In certain embodiments, a cMUT with a 2D phased array can be configured as described in U.S. Pat. No. 5,520,187, issued to Snyder, or U.S. Pat. No. 5,897,501, issued to Wildes et al., for example.

The elevational rows can be used in conjunction with the elevational biasing circuitry of the cMUT. One or more elevation delay profiles can be computed for the columns of elements. Then, elevation delay and/or azimuthal delay can be applied to the transmit and/or receive signal for each element using standard (prior-art) transmit and receive beamformers in the system front end 20. Applying elevation delay and/or azimuthal delay in such a way can improve the sensitivity of beams steered in elevation away from orthogonal to the array, while also improving the spreading of short pulsed excitations or echoes. However, resulting beams can still have large sidelobes due to the coarseness of the phase information and large temporal misalignment of pulses, either of which can result in reduced image quality.

In certain embodiments of the present technology, biasing control can then be provided by applying focusing functions, as described below, for example, which can result in a residual phase with an elevational scale that is finer than the coarse elevational element rows. There can be several bias rows per element row. Such improvements can result in improved beam patterns and, thus, improved image quality.

In certain embodiments, the front-end 20 can create one or more acoustic lines, corresponding to one or more receive beams, for each transmit beam. For example, in certain embodiments, a transmitter can transmit an ultrasonic beam emitted from the transducer 10. The transmitted ultrasonic beam can then be reflected from a subject, such as a patient, for example. The reflected beam can then be detected by the transducer 10 and received by a receiver. The receiver can acquire an acoustic line for the received ultrasonic beam. This acoustic line can be combined with acoustic lines from previous transmissions and/or acoustic lines from later transmissions to generate a composite acoustic line with desired characteristics. For example, in certain embodiments, a beamformer can combine any number of acoustic lines to create a beam pattern that can be used to generate images. In certain embodiments, a conventional multi-line acquisition ("MLA") capable receive beamformer with multiple receive delay per elevational element can be used to provide multiple beams in the elevational direction as well as the azimuthal direction.

In certain embodiments, the front-end 20 can utilize two transmissions per composite acoustic line. For example, in certain embodiments, the two transmissions can have identical transmit elevation aperture functions and amplitude modulated pulse-wave excitations that are shifted 90 degrees in phase relative to each other within the same envelope (also referred to as a quadrature relationship). Then, two receive elevation aperture functions can be used in reception of the echoes resulting from the two transmissions. These two receive elevation aperture functions can include focusing functions, and, optionally, a traditional apodization function, such as a Hamming, Hanning, Tukey or Gaussian apodization function, for example.

Focusing functions can be used to provide the desired phase for a given element at a selected center frequency within the precision of practical quantization. In certain embodiments, focusing functions can include Hilbert-Fresnel functions. For example, in certain embodiments, two receive elevation aperture functions can include the Hilbert-Fresnel functions below, where $AI_i$ is the amplitude from bias during in-phase transmission, $AQ_i$ is the amplitude from bias during quadrature transmission, $\omega_c$ is the center frequency of a transmission in radians/second, and $d_i$ is beamforming delay in seconds.

$$AI_i = \cos(-\omega_c d_i)$$

$$AQ_i = \sin(-\omega_c d_i)$$

A first acoustic line can be acquired using the first function of the pair for receive. A second acoustic line can be acquired using the second function of the pair for receive of elevation apertures. Combining the two acoustic lines can cancel the undesired sidelobes while retaining and/or reinforcing the desired main lobe. Cancelling the undesired sidelobes while retaining and/or reinforcing the desired main lobe can result in an improved beam pattern that can be used to generate images.

Applying the pair of Hilbert-Fresnel functions, as described above, can have the desired effect because the functions are related to each other by a Hilbert Transform. That is, the Fourier transforms of the functions are nearly identical in magnitude but have inverted polarity on one side of the spectrum, and a quadrature phase relationship (that is, a 90 degree phase rotation). In the case of a far-field focus, with a linear relationship between the transducer position and the delay, the receive elevation aperture functions become the scaled Hilbert-Fresnel functions, and the resulting far-field beam patterns, in sine-angle space, become the Fourier transforms of the Hilbert-Fresnel functions. This can be deduced from Fresnel approximations of the Huygens-Fresnel Principle. Due to this relationship, quadrature excitation can compensate for the 90 degree phase rotation in the two acoustic lines.

The same approach described above for reception, can be used for transmission. For example, in certain embodiments, two quadrature related transmissions can use the pair of Hilbert-Fresnel functions described above for the transmit elevation apertures with receive apertures that are the same for both receptions. The resulting acoustic lines can then be combined to produce an improved beam pattern, which can then be used to generate an image.

The reception and transmission approaches described above can be used together to produce a two-way (transmit and receive) beam pattern by combining four acoustic lines that result from four permutations of transmit and receive function pairs. For example, in certain embodiments, the front-end 20 can form a composite acoustic line with a two-way beam pattern utilizing two transmissions. This two-way focusing approach can leverage the same Fourier transform relationship between the aperture and the beam response, as described above, to create a two-way beam that is the product of the transmit and receive beam patterns. If the same aperture (apodization) function, A, is used for both transmit and receive apertures, then the two-way beam pattern is the square of the Fourier transform of the aperture function $F^2(A)$.

To apply two-transmission two-way focusing, focusing functions can be created that have the square of their Fourier Transforms approximately the same but inverted on one half. For example, in certain embodiments, focusing functions used to produce a two-way beam pattern can include the Hilbert-Fresnel functions below, where $AI_i$ is the amplitude from bias during in-phase transmission, $AQ_i$ is the amplitude from bias during quadrature transmission, $\omega_c$ is the center frequency of a transmission in radians, and $d_i$ is beamforming delay in seconds.

$$AI_i = \cos(-\omega_c d_i)$$

$$AQ_i = \mathrm{sqrt}(0.5)*[\cos(-\omega_c d_i)+\sin(-\omega_c d_i)]$$

A first acoustic line is acquired using the first function of the pair for transmit and receive. A second acoustic line is acquired using the second function of the pair for transmit and receive of elevation apertures. Combining the two acoustic lines can create an improved beam pattern that can then be used to generate images.

Experiments applying Hilbert-Fresnel functions in connection with a cMUT with a 2D phased array, as described above, have been conducted and have resulted in improved beam patterns. Such experiments confirmed a theoretical analysis of beam pattern improvement in ideal systems. Also, in practice, some quantization of phase ($-\omega_c d_i$) and amplitudes (A) can be performed.

The theoretical illustration for the idealized case of a continuous wave excitation (as opposed to a pulsed wave excitation) and an infinite aperture is provided below. The equations below show this relationship where $BSi(t)$ is the in-phase beam summation, $BSq(t)$ is the quadrature beam summation, t is time in seconds, s is the angular position in beam space in units of sin(theta) and sf is the focus angle.

$$BSi(t)=\Sigma_i AI_i * \sin(\omega_c(t-d_i))$$

$$BSq(t)=\Sigma_i AQ_i * \sin(\omega_c(t-d_i)+\pi/2)$$

The one-way beam pattern is the Fourier transform of the aperture.

$$F(AI_i)=0.5*[\delta(s+sf)+\delta(s-sf)]$$

$$F(AQ_i)=0.5*\mathrm{sqrt}(0.5)*[(1-i)*\delta(s+sf)+(1+i)*\delta(s-sf)]$$

The two-way beam pattern is the square of the one-way pattern.

$$F(AI_i)^2=0.25*[\delta(s+sf)+\delta(s-sf)]$$

$$F(AQ_i)^2=0.25*i[-\delta(s+sf)+\delta(s-sf)]$$

The $\pi/2$ phase shift in the quadrature transmit signal, produces a quadrature beam response that will cancel the undesired sidelobes while retaining and/or reinforcing the desired main lobe.

$$F(AQ_i)^2 - i*F(AQ_i)^2 = 0.25*[\delta(s+sf)+\delta(s-sf)], +0.25[-\delta(s+sf)+\delta(s-sf)]=0.5*\delta(s-sf),$$

which is the desired result.

Once a beam pattern has been focused, as described above, the beam pattern can be output from the front-end 20 to the imaging mode processor 30 in the form of digital signal data. The imaging mode processor 30 can process the received digital signal data to produce estimated parameter values. The estimated parameter values can be produced using the received digital signal data. The digital signal data can be analyzed in frequency bands centered at the fundamental, harmonics, or sub-harmonics of the transmitted signals to produce the estimated parameter values. The imaging mode processor 30 can provide amplitude detection, data compression, and other processing for an imaging mode, such as B-mode imaging, M-mode imaging, BM-mode imaging, harmonic imaging, Doppler imaging, color flow imaging, and/or any other ultrasound imaging mode. The imaging mode processor 30 can pass the estimated parameter values to a control processor 50 over the digital bus 70. The imaging mode processor 30 can also pass the estimated parameter values to the display 75 via the digital bus 70.

The display 75 can include a display processor 80 and a monitor 90. The display processor 80 can accept digital parameter values from the imaging mode processor 30 and the control processor 50. The display processor 80 can perform scan-conversion functions, color mapping functions, and tissue/flow arbitration functions, for example. The display processor 80 can process map and format the digital data for display, convert the digital display data to analog display signals, and pass the analog display signals to the monitor 90. The monitor 90 can accept the analog display signals from the display processor 80 and display the resulting image. An operator may view the image on the monitor 90.

The control processor 50 is the central processor of the ultrasound imaging system 100. The control processor 50 can interface with other components of the ultrasound imaging system 100 using the digital bus 70. The control processor 50 can execute various data algorithms and functions for various imaging and diagnostic modes. Digital data and commands can be transmitted and received between the control processor 50 and other components of the ultrasound imaging system 100. In certain embodiments, functions performed by the control processor 50 can be performed by multiple processors and/or can be integrated into the imaging mode processor 30 and/or the display processor 80. In another embodiment, the functions of the processors 30, 50, and 80 can be integrated into a single personal computer ("PC") backend.

The user interface 60 can allow user commands to be input by the operator to the ultrasound imaging system 100 through the control processor 50. The user interface 60 can include a keyboard, mouse, switches, knobs, buttons, track ball, and/or on screen menus, for example.

Figure 2:
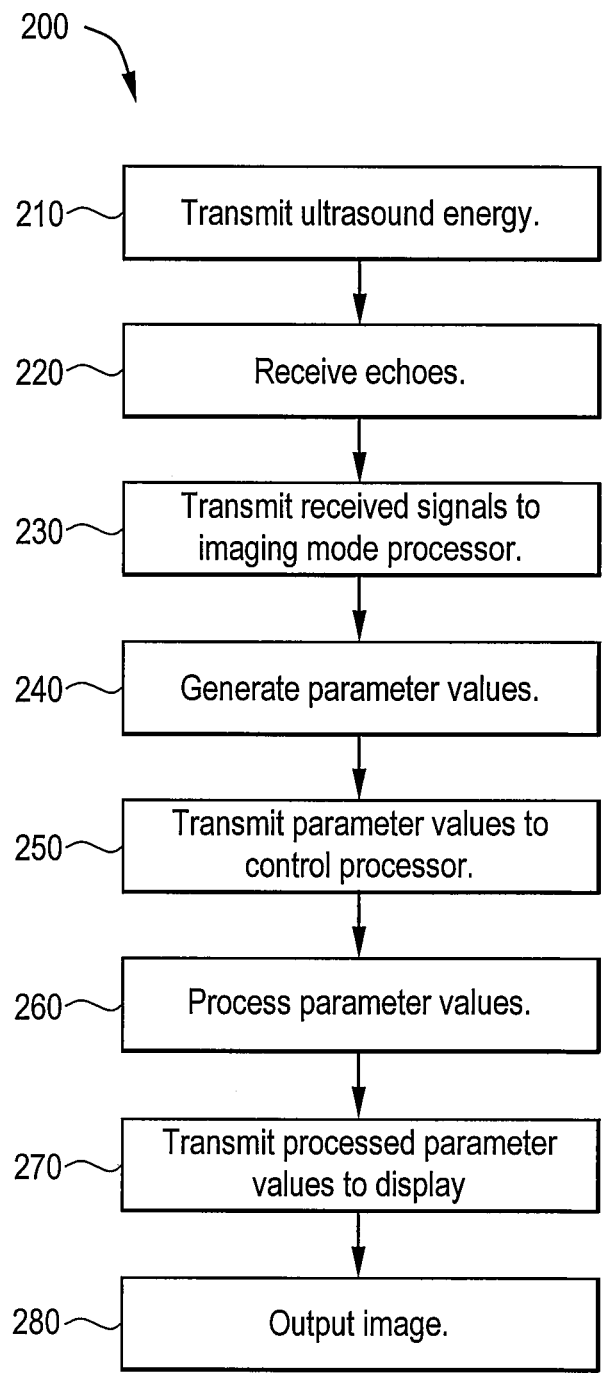
FIG. 2 illustrates a method for ultrasound imaging used in accordance with an embodiment of the present technology.

FIG. 2 illustrates a method 200 for ultrasound imaging used in accordance with an embodiment of the present technology. At 210, ultrasound energy is transmitted. For example, in certain embodiments, a transducer transmits ultrasound energy into a subject, such as a patient. For example, in certain embodiments, the ultrasound energy that is transmitted by the transducer can be transmitted in accordance with any of the focusing approaches described in connection with FIG. 1.

At 220, ultrasound energy or echoes backscattered from the subject are received. For example, in certain embodiments, ultrasound energy or echoes backscattered from the subject are detected by a transducer and signals are received at a front-end in response to ultrasound waves backscattered from the subject. For example, in certain embodiments, the ultrasound energy that is received can be received in accordance with any of the focusing approaches described in connection with FIG. 1.

At 230, the received signals are transmitted to an imaging mode processor. For example, in certain embodiments, the received signals are transmitted from a front-end to an imaging mode processor using a digital bus. At 240, parameter values are generated. For example, in certain embodiments, an imaging mode processor generates parameter values based on the received signals.

At 250, the parameter values are sent to a control processor. For example, in certain embodiments, the parameter values are transmitted from an imaging mode processor to a control processor using a digital bus. At 260, parameter values are processed. For example, in certain embodiments, a control processor processes the parameter values for use in display, storage and diagnostics at a display. In certain embodiments, the control processor processes the image data parameter values to reduce artifacts and process resulting image(s), for example.

At 270, processed parameter values are transmitted. For example, in certain embodiments, processed parameter values are transmitted to a display. In certain embodiments, a display processor can also process parameter values from a plurality of focal zone images to produce a combined image in conjunction with and/or in addition to the control processor, for example.

At 280, an image is output. For example, in certain embodiments, a diagnostic image is produced and output at a monitor. In certain embodiments, the image may be stored, displayed, printed and/or further transmitted, for example. In certain embodiments, the display processor can produce the diagnostic image using the processed parameter values from the digital signal data.

Applying the method 200 as described above, and/or in light of the embodiments described in connection with FIG. 1, can decrease sidelobe size and/or temporal misalignment of pulses, thereby providing improved image quality.

While the invention has been described with reference to embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. An ultrasonic imaging system comprising:
a transducer configured to emit a first ultrasonic beam and a second ultrasonic beam and detect a reflection of the first ultrasonic beam and the second ultrasonic beam, wherein the second emitted ultrasonic beam and the first emitted ultrasonic beam comprise a quadrature relationship;
a receiver configured to:
receive the reflection of the first ultrasonic beam and the reflection of the second ultrasonic beam from the transducer, and
use a first focusing function to acquire a first acoustic line of the reflection of the first ultrasonic beam and use a second focusing function to acquire a second acoustic line of the reflection of the second ultrasonic beam; and
a beamformer configured to combine the first acoustic line and the second acoustic line to create a beam pattern.

2. The system of claim 1, wherein the first focusing function comprises $AI_i = \cos(-\omega_c d_i)$ and the second focusing function comprises $AQ_i = \sin(-\omega_c d_i)$, wherein $AI_i$ represents an amplitude from bias during transmission of the first ultrasonic beam, $AQ_i$ represents an amplitude from bias during transmission of the second ultrasonic beam, ωc represents a center frequency of a transmission in radians/second, and di represents a beamforming delay in seconds.

3. The system of claim 1, wherein the transducer comprises a Capacitive Micromachined Ultrasonic Transducer.

4. The system of claim 1, wherein the transducer comprises a two dimensional phased array transducer including a plurality of elements in elevational rows.

5. The system of claim 1, wherein the beamformer comprises a multi-line acquisition capable receive beamformer.

6. The system of claim 1, further comprising a transmitter configured to:

transmit the first ultrasonic beam to the transducer through an analog bus using the first focusing function; and transmit the second ultrasonic beam to the transducer through the analog bus using the second focusing function.

7. The system of claim 6, wherein the first focusing function comprises $AI_i = \cos(-\omega_c d_i)$ and the second focusing function comprises $AQ_i = \text{sqrt}(0.5)*[\cos(-\omega_c d_i) + \sin(-\omega_c d_i)]$, wherein AIi represents an amplitude from bias during transmission of the first ultrasonic beam, AQi represents an amplitude from bias during transmission of the second ultrasonic beam, $\omega c$ represents a center frequency of a transmission in radians/second, and di represents a beamforming delay in seconds.

8. A method for creating a beam pattern, the method comprising:
   emitting a first ultrasonic beam from at least one transducer;
   emitting a second ultrasonic beam comprising a quadrature relationship with respect to the first ultrasonic beam;
   receiving a reflection of the first ultrasonic beam and the second ultrasonic beam;
   using a first focusing function to acquire a first acoustic line of the reflection of the first ultrasonic beam and using a second focusing function to acquire a second acoustic line of the reflection of the second ultrasonic beam; and
   combining the first and second acoustic lines to create a beam pattern.

9. The method of claim 8, wherein the first focusing function comprises $AI_i = \cos(-\omega_c d_i)$ and the second focusing function comprises $AQ_i = \sin(-\omega_c d_i)$, wherein AIi represents an amplitude from bias during transmission of the first ultrasonic beam, AQi represents an amplitude from bias during transmission of the second ultrasonic beam, $\omega c$ represents a center frequency of a transmission in radians/second, and di represents a beamforming delay in seconds.

10. The method of claim 8, wherein the first ultrasonic beam is emitted using the first focusing function and the second ultrasonic beam is emitted using the second focusing function.

11. The system of claim 10, wherein the first focusing function comprises $AI_i = \cos(-\omega_c d_i)$ and the second focusing function comprises $AQ_i = \text{sqrt}(0.5)*[\cos(-\omega_c d_i) + \sin(-\omega_c d_i)]$, wherein AIi represents an amplitude from bias during transmission of the first ultrasonic beam, AQi represents an amplitude from bias during transmission of the second ultrasonic beam, $\omega c$ represents a center frequency of a transmission in radians/second, and di represents a beamforming delay in seconds.

12. The method of claim 8, further comprising using the beam pattern to generate an image.

13. A method for ultrasonic imaging, the method comprising:
   biasing a plurality of elevational elements in an ultrasonic transducer with a corresponding plurality of first amplitudes $AI_i$;
   emitting a first ultrasonic beam from the plurality of elevational elements at the first amplitudes;
   biasing the plurality of elevational elements with a corresponding plurality of second amplitudes;
   emitting a second ultrasonic beam from the plurality of elevational elements at the second amplitudes;
   receiving reflections of the first ultrasonic beam and the second ultrasonic beam;
   using a first focusing function according to the first amplitudes to acquire a first acoustic line of the reflection of the first ultrasonic beam;
   using a second focusing function according to the second amplitudes to acquire a second acoustic line of the reflection of the second ultrasonic beam; and
   combining the first and second acoustic lines to create a beam pattern.

14. The method of claim 13, wherein the first ultrasonic beam and the second ultrasonic beam comprise a quadrature relationship.

15. The method of claim 14, wherein the first focusing function defines a relationship between the first amplitudes and $\cos(-\omega_c d_i)$;
   wherein the second focusing function defines a relationship between the second amplitudes and $\sin(-\omega_c d_i)$; and
   wherein $\omega c$ represents a center frequency of a transmission in radians/second, and di represents a beamforming delay in seconds for each of the plurality of elevational elements.

* * * * *